United States Patent

Wingert et al.

[11] Patent Number: 6,133,451
[45] Date of Patent: Oct. 17, 2000

[54] METHOD FOR PRODUCING 2-(3-PYRAZOLYL-OXYMETHYLENE) NITROBENZENES

[75] Inventors: Horst Wingert, Mannheim; Norbert Götz, Worms; Michael Keil, Freinsheim; Ralf Klintz, Grünstadt; Uwe Josef Vogelbacher, Ludwigshafen; Josef Wahl, Schifferstadt, all of Germany

[73] Assignee: BASF Aktiengesellschaft, Ludwigshafen, Germany

[21] Appl. No.: 09/463,564

[22] PCT Filed: Jul. 20, 1998

[86] PCT No.: PCT/EP98/04490

§ 371 Date: Jan. 27, 2000

§ 102(e) Date: Jan. 27, 2000

[87] PCT Pub. No.: WO99/06373

PCT Pub. Date: Feb. 11, 1999

[30]   Foreign Application Priority Data

Jul. 30, 1997 [DE] Germany .................. 197 32 692

[51] Int. Cl.$^7$ .................................................. C07D 231/22
[52] U.S. Cl. ............................................................ 548/371.1
[58] Field of Search ........................................... 548/371.1

[56]   References Cited

FOREIGN PATENT DOCUMENTS 26 14 485  10/1976  Germany .
WO96/01256  1/1996  WIPO .

OTHER PUBLICATIONS

Recueil des Travaux (Chimiques des Pays–Bas, Bd., 107/2, 1988 73–81, van den Berge et al.

Primary Examiner—Robert W. Ramsuer
Attorney, Agent, or Firm—Keil & Weinkauf

[57]   ABSTRACT

2-(3-Pyrazolyloxymethylene)nitrobenzene [sic] derivatives of the formula I

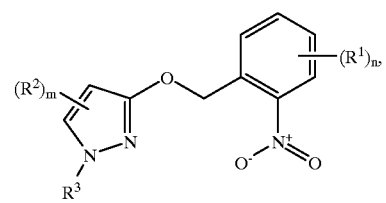

where the substituents and indices have the meanings given in the description, are prepared by bromination of an o-nitrotoluene of the formula II

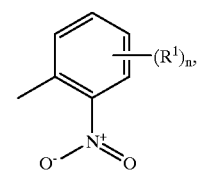

and subsequent reaction with a 3-hydroxypyrazole of the formula IV

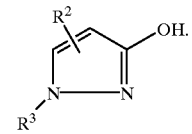

8 Claims, No Drawings

METHOD FOR PRODUCING 2-(3-PYRAZOLYL-OXYMETHYLENE) NITROBENZENES

This application is a 371 of PCT/EP98/04490 filed Jul. 20, 1998.

The present invention relates to a process for preparing 2-(3-pyrazolyloxymethylene)nitrobenzene derivatives of the formula I

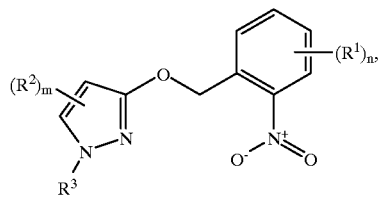

where $R^1$ is halogen;
  unsubstituted or substituted alkyl or alkoxy;
$R^2$ is cyano, halogen, alkyl, haloalkyl, alkoxy, alkylthio or alkoxycarbonyl;
$R^3$ is unsubstituted or substituted alkyl, alkenyl or alkynyl;
  unsubstituted or substituted saturated or mono- or diunsaturated carbocyclyl or heterocyclyl;
  unsubstituted or substituted aryl or hetaryl;
m is 0, 1 or 2, it being possible for the substituents $R^2$ to be different when m is greater than 1;
n is 0, 1, 2, 3 or 4, it being possible for the substituents $R^1$ to be different when n is greater than 1;

by bromination of an o-nitrotoluene of the formula II

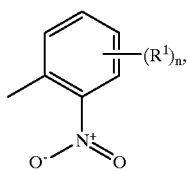

where $R^1$ has the abovementioned meaning, to give the o-nitrobenzyl bromide of the formula III

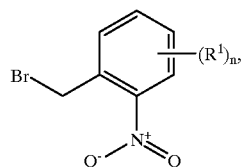

in the presence of a nonpolar aprotic solvent and subsequent reaction of the resulting solution of III with a 3-hydroxypyrazole of the formula IV

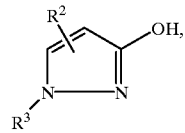

where $R^2$ and $R^3$ have the abovementioned meanings, in the presence of a base.

Numerous processes for preparing o-nitrobenzyl bromides of the formula III starting from o-nitrotoluene derivatives II are described in the literature. In many cases, owing to the deactivation by the nitro group, the side-chain bromination takes place only at temperatures above 100° C. and under pressure. These conditions are disadvantageous in view of the low thermal stability of the o-nitrobenzyl bromides and are problematic in terms of industrial safety (see Z. Chem. 12 (1972) 139).

WO 96/01256 describes the preparation of 2-(3-pyrazolyloxy-methylene)nitrobenzene derivatives I starting from o-nitrobenzyl bromides III in general. No details are given of the industrial preparation of III in this publication. Nor does the publication provide any help with safe handling of III on implementation of the described process on the industrial scale. The handling of industrial quantities of III is problematic because of the lachrymatory and mucosal-irritant effect of III and the thermal instability of III which has already been mentioned.

It is an object of the present invention to find a route to 2-(3-pyrazolyloxymethylene)nitrobenzene derivatives I which is industrially applicable and, on the one hand, solves the difficult operating and safety problems in handling III and, on the other hand, provides the required product I in good yield and purity. Compounds of the formula I are important intermediates for preparing inter alia the fungicidal agents described in WO 96/01256.

We have found that this object is achieved by the process mentioned at the outset, wherein the solution of the o-nitrobenzyl bromide III resulting from the bromination is reacted further with IV, in the solvent used, directly without intermediate isolation of the o-nitrobenzyl bromide III.

Surprisingly, the novel process provides the required compound I in good yield and in excellent purity. This was not to be expected since the bromination always takes place with formation of considerable quantities of o-nitrobenzal bromide V, which is able to react with 3-hydroxypyrazoles IV to give bis-O-alkylated acetals of the formula VI.

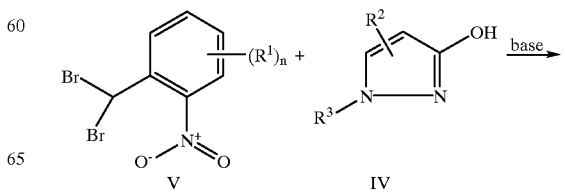

-continued

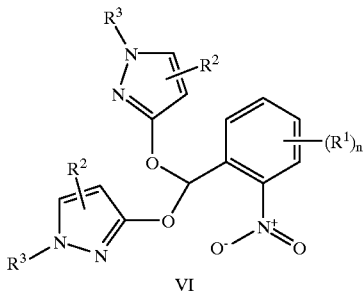

VI

The formation of VI can be virtually completely suppressed by employing the 3-hydroxypyrazole IV, which is the more costly component, in equimolar quantities, or even less, relative to the o-nitrobenzyl bromide III. The selectivity of the alkylation reaction is surprising; on the contrary, the substrates o-nitrobenzyl bromide III and o-nitrobenzal bromide V would have been assumed to be of comparable reactivity.

The novel process can be used to prepare 2-(3-pyrazolyloxy-methylene)nitrobenzene derivatives of the formula I. The meanings specified above for the substituents $R^1$ to $R^3$ in formula I represent collective terms for individual lists of single members of the groups. All alkyl moieties may be straight-chain or branched. Halogenated substituents preferably have from 1 to 6 identical or different halogen atoms.

Examples of specific meanings are:

halogen: fluorine, chlorine, bromine and iodine;

alkyl or the alkyl moieties of alkoxy, alkoxycarbonyl and alkylthio: saturated, straight-chain or branched hydrocarbon radicals, in particular having 1 to 10 carbon atoms, eg. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

alkenyl: unsaturated, straight-chain or branched hydrocarbon radicals, in particular having 2 to 10 carbon atoms and one double bond at any position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched hydrocarbon groups, in particular having 2 to 20 carbon atoms and one triple bond at any position, eg. $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl-, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

haloalkyl: straight-chain or branched alkyl groups having 1 to 4 carbon atoms (as mentioned above), it being possible for the hydrogen atoms in these groups to be partly or completely replaced by halogen atoms as specified above, eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

saturated or mono- or diunsaturated carbocyclyl or heterocyclyl: for example carbocycles such as cyclopropyl, cyclopentyl, cyclohexyl, 2-cyclopentenyl, 2-cyclohexenyl or heterocyclyl such as 2-tetrahydrofuranyl, 2-tetrahydrothienyl, 2-pyrrolidinyl, 3-isoxazolidinyl, 3-isothiazolidinyl, 1,3,4-oxazolidin-2-yl, 2,3-dihydro-2-thienyl, 4,5-isoxazolin-3-yl, 3-piperidinyl, 1,3-dioxan-5-yl, 4-piperidinyl, 2-tetrahydropyranyl, 4-tetrahydropyranyl;

aryl or hetaryl: for example phenyl and naphthyl, preferably phenyl or 1- or 2-naphthyl, and hetaryl radicals, for example 5-membered heteroaromatic rings containing one to three nitrogen atoms and/or one oxygen or sulfur atom such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,5-triazol-3-yl, 1,2,3-triazol-4-yl, 1,2,3-triazol-5-yl, 1,2,3-triazol-4-yl, 5-tetrazolyl, 1,2,3,4-thiatriazol-5-yl and 1,2,3,4-oxatriazol-5-yl, in particular 3-isoxazolyl, 5-isoxazolyl, 4-oxazolyl, 4-thiazolyl, 1,3,4-oxadiazol-2-yl and 1,3,4-thiadiazol-2-yl;

"unsubstituted or substituted" referring to alkyl, alkenyl and alkynyl groups and referring to aryl and hetaryl is intended to express the fact that these groups may be partly or completely halogenated (ie. the hydrogen atoms in these groups can be partly or completely replaced by identical or different halogen atoms as mentioned above (preferably fluorine, chlorine and bromine, in particular fluorine and chlorine)) and/or may carry one to three, in particular one, of the following radicals:

$C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylamino, di-$C_1$–$C_6$-alkylamino, $C_2$–$C_6$-alkenyloxy, $C_2$–$C_6$-haloalkenyloxy, $C_2$–$C_6$-alkynyloxy, $C_2$–$C_6$-haloalkynyloxy, $C_3$–$C_6$-cycloalkyl, $C_3$–$C_6$-cycloalkoxy, $C_3$–$C_6$-cycloalkenyl, $C_3$–$C_6$-cycloalkenyloxy, $C_1$–C6-alkylcarbonyl, $C_1$–$C_6$-alkoxycarbonyl, $C_1$–$C_6$-alkylaminocarbonyl, di-$C_1$–$C_6$-alkylaminocarbonyl, $C_1$–$C_6$-alkylcarbonyloxy, $C_1$–$C_6$-alkylcarbonylamino. Aryl and hetaryl may carry, in addition to those already mentioned, one to three of the following radicals: $C_1$–$C_6$-alkyl and $C_1$–$C_6$-haloalkyl.

Suitable solvents for the novel process are those which are inert during the bromination and the subsequent alkylation, for example aromatic hydrocarbons such as benzene, tert-butylbenzene, tert-amylbenzene, or halogenated hydrocarbons such as methylene chloride, 1,2-dichloroethane, chloroform, tetrachloromethane, ortho- or para-dichlorobenzene, 1,2,4-trichlorobenzene and, in particular, chlorobenzene.

The ortho-nitrotoluenes II employed in the novel process can in most cases be purchased or are obtainable in a simple manner by known processes (eg. Organikum Barth Verlagsgesellschaft (1993) 320 et seq.).

The brominating agents which can be employed for brominating the ortho-nitrotoluenes II are elemental bromine or bromine salts such as sodium bromide inter alia, and hydrogen bromide, preferably in the form of hydrobromic acid, the last two preferably being used in the presence of an oxidizing agent. A technical azeotropic mixture of hydrobromic acid (about 47% strength) is particularly preferred.

Examples of oxidizing agents suitable for oxidizing hydrogen bromide or bromide ions are peracids, peroxides, chlorine bleaching solution, chlorine, sodium bromate and potassium peroxodisulfate, and hydrogen peroxide is particularly suitable.

In a preferred embodiment of the novel process, the amounts of oxidizing agent used are such that the hydrogen bromide formed in the reaction is also reoxidized. Preferably from 1.5 to 2.0 equivalents of the oxidizing agent are added per bromide equivalent. If, on the other hand, elemental bromine is used as source of bromine, it is also possible to dispense with the use of an oxidizing agent or else, if it is wished to oxidize the hydrogen bromide formed in the reaction, it is sufficient to add from 0.5 to 1.0 equivalent (based on bromine) of an oxidizing agent. It is possible in this way almost to halve the amount of brominating agent used.

The brominating agent is generally employed in a molar ratio of 0.7–1.3, and preferably in a molar ratio of 0.9–1.0, to the o-nitrotoluene II.

Initiators preferred for generating the bromine free radicals which are required for the reaction in the novel process are azo compounds such as azocarboxylic esters and azocarbonitriles. Azoisobutyronitrile is particularly preferably used.

The initiators are generally added in a concentration of from 0.1 to 20 mol %, based on the o-nitrololuene [sic] (II), and preferably in a concentration of from 1 to 10 mol %, to the reaction mixture.

The bromination is carried out at from 20 to 100° C., preferably from 20 to 80° C. The optimal reaction temperature depends firstly on the thermal stability of the o-nitrotoluene II and the product III obtained therefrom, and secondly on the initiator decomposition temperature. The following table summarizes various initiators with their structures and 10 h half-life decomposition temperatures. The reaction is preferably carried out slightly above or below the 10 h half-life decomposition temperature of the initiator (±10° C.).

TABLE

| Designation | Name | Structure | 10 h Half-life decomposition temperature |
|---|---|---|---|
| A | 2,2'-Azobis(4-methoxy-2,4-dimethylvaleronitrile) | $CH_3-\underset{\underset{CH_3}{\mid}}{\overset{\overset{OCH_3}{\mid}}{C}}-CH_2-\underset{\underset{CN}{\mid}}{\overset{\overset{CH_3}{\mid}}{C}}-N{=}N-\underset{\underset{CN}{\mid}}{\overset{\overset{CH_3}{\mid}}{C}}-CH_2-\underset{\underset{CH_3}{\mid}}{\overset{\overset{OCH_3}{\mid}}{C}}-CH_3$ | 30° C. |
| B | 2,2'-Azobis(2-cyclopropylpropionitrile) | cyclopropyl–$\underset{\underset{CN}{\mid}}{\overset{\overset{CH_3}{\mid}}{C}}$–N=N–$\underset{\underset{CN}{\mid}}{\overset{\overset{CH_3}{\mid}}{C}}$–cyclopropyl | 42° C. |
| C | 2,2'-Azobis(2,4-dimethylvaleronitrile) | $CH_3-\underset{\underset{CH_3}{\mid}}{CH}-CH_2-\underset{\underset{CN}{\mid}}{\overset{\overset{CH_3}{\mid}}{C}}-N{=}N-\underset{\underset{CN}{\mid}}{\overset{\overset{CH_3}{\mid}}{C}}-CH_2-\underset{\underset{CH_3}{\mid}}{CH}-CH_3$ | 51° C. |
| D | 2,2'-Azobis(2-methylpropionitrile) | $CH_3-\underset{\underset{CN}{\mid}}{\overset{\overset{CH_3}{\mid}}{C}}-N{=}N-\underset{\underset{CN}{\mid}}{\overset{\overset{CH_3}{\mid}}{C}}-CH_3$ | 65° C. |

TABLE-continued

| Designation | Name | Structure | 10 h Half-life decomposition temperature |
|---|---|---|---|
| E | Dimethyl-2'2'-azobis(2-methyl-propionate) | $CH_3-\underset{COOCH_3}{\overset{CH_3}{\underset{|}{\overset{|}{C}}}}-N=N-\underset{COOCH_3}{\overset{CH_3}{\underset{|}{\overset{|}{C}}}}-CH_3$ | 66° C. |
| F | 2,2'-Azobis(2-methyl-butyronitrile) | $CH_3-CH_2-\underset{CN}{\overset{CH_3}{\underset{|}{\overset{|}{C}}}}-N=N-\underset{CN}{\overset{CH_3}{\underset{|}{\overset{|}{C}}}}-CH_2-CH_3$ | 67° C. |
| G | 1,1'-Azobis(cyclo-hexan-1-carbonitrile) | (cyclohexyl)(CN)C—N=N—C(CN)(cyclohexyl) | 88° C. |

The bromination is preferably carried out in a two-phase system. The two-phase system generally comprises the solution of the bromine salt in water or preferably the hydrobromic acid together with the solvent used and, where appropriate, the initiator or a part-quantity of the initiator. The mixture is brought to the reaction temperature and then the nitrotoluene II is metered in, in the presence or absence of the initiator, continuously or in portions over the course of from a half up to several hours. The metering in of II generally takes place in parallel with the metering in of the oxidizing agent so that no excess bromine is present in the reaction mixture. It is likewise possible to mix the substrate II with the brominating agent and the initiator and to control the reaction by the metering in of the oxidizing agent.

When bromine is used as source of bromine, the procedure is generally similar to that described but bromine is metered in to a mixture of water and solvent, with or without initiator. With this procedure, the substrate II can be present from the outset or be metered in.

If stable oxidizing agents are used, they can be mixed with the substrate II, and the course of the reaction can be controlled by adding the bromine component.

The bromination can be carried out batchwise and, preferably, continuously. The continuous procedure has the advantage that the dimensions of the apparatus are smaller, and thus smaller amounts of solutions containing the substrate II are kept at elevated temperature. Because II is extremely thermally unstable, the continuous process thus has an advantage in terms of industrial safety.

When the metering in is complete, the reaction mixture is usually kept at the chosen reaction temperature for from 0.5 to 3 hours. The organic phase is then separated off and employed, without further purification and drying, in the alkylation stage.

The solvent used in the alkylation stage is the same as in the bromination step. It is possible to add a polar solvent for this stage.

The 3-hydroxypyrazoles IV are known from the literature or can be prepared by methods described therein (eg. Chem. Pharm. Bull. 19 (1971) 1389–1394). The compounds IV are obtained in a particularly advantageous manner by the processes described in WO 97/03939, EP-A 680 945 and DE App. No. 19 652 516.0. The 3-hydroxypyrazoles which are formed can in some cases be subjected to the subsequent alkylation directly as aqueous solutions.

The alkylation of IV with the o-nitrobenzyl bromides III is generally carried out at from 20 to 90° C. and preferably from 40 to 80° C.

The o-nitrobenzyl bromide III is generally employed in a molar ratio of 0.9–1.3, preferably in a molar ratio of 1.0–1.2, relative to IV.

Bases which are generally suitable are inorganic compounds such as alkali metal and alkaline earth metal hydroxides (eg. lithium hydroxide, sodium hydroxide, potassium hydroxide and calcium hydroxide), alkali metal and alkaline earth metal oxides (eg. lithium oxide, sodium oxide, calcium oxide and magnesium oxide), alkali metal and alkaline earth metal hydrides (eg. lithium hydride, sodium hydride, potassium hydride and calcium hydride), alkali metal amides (eg. lithium amide, sodium amide and potassium amide), alkali metal and alkaline earth metal carbonates (eg. lithium carbonate and calcium carbonate) and alkali metal bicarbonates (eg. sodium bicarbonate), organometallic compounds, in particular alkali metal alkyls (eg. methyllithium, butyllithium and phenyllithium), alkylmagnesium halides (eg. methylmagnesium chloride) and alkali metal and alkaline earth metal alcoholates (eg. sodium methanolate, sodium ethanolate, potassium ethanolate, potassium tert-butanolate and dimethoxymagnesium), also organic bases, eg. tertiary amines such as trimethylamine, triethylamine, diisopropylethylamine and N-methylpiperidine, pyridine, substituted pyridines such as collidine, lutidine and 4-dimethylaminopyridine, and bicyclic amines.

Sodium hydroxide and potassium hydroxide are particularly preferred.

The bases are generally used in equimolar quantities, in excess or, where appropriate, as solvents.

It may be advantageous for the reaction to add a catalytic amount of a crown ether (eg. 18-crown-6 or 15-crown-5).

The reaction can also be carried out in two-phase systems consisting of a solution of alkali metal or alkaline earth metal hydroxides or carbonates in water and of an organic phase (eg. aromatic and/or halogenated hydrocarbons). Suitable phase-transfer catalysts in this case are, for example, ammonium halides and tetrafluoroborates (eg. benzyltriethylammonium chloride, benzyltributylammonium bromide, tetrabutylammonium chloride, hexadecyltrimethylammonium bromide or tetrabutylammonium tetrafluoroborate) and phosphonium halides (eg. tetrabutylphosphonium chloride and tetraphenylphosphonium bromide). Tetrabutylammonium bromide, hydroxide and bisulfate are particularly preferred.

It may be advantageous for the reaction initially to convert the 3-hydroxypyrazole with the base into the corresponding hydroxylate, which is then reacted with the benzyl derivative.

The alkylation step can also be carried out batchwise or continuously.

PROCESS EXAMPLES

The novel process will be explained in detail taking the example of the synthesis of 2-[(N-p-chlorophenyl)-3-pyrazolyloxy-methyl]nitrobenzene Ia by
a) bromination of ortho-nitrotoluene IIa and
b) reaction of the resulting ortho-nitrobenzyl bromide IIIa with 3-hydroxy-N-(p-chlorophenyl)pyrazole IVa.

Example 1 a) Preparation of o-nitrobenzyl bromide

A solution of 6.6 g (1 mol % based on hydrobromic acid) of azoisobutyronitrile (AIBN) in 1350 g of chlorobenzene was mixed with 620 g (3.6 mol) of 47% strength hydrobromic acid in a 2.5 liter flat flange flask with impeller stirrer (300 rpm) and baffle. The contents of the reactor were heated, to 75° C. After this temperature was reached, feeds I and II were fed in by two metering pumps.

Feed I: a solution of 26.2 g (4 mol %) of AIBN in 548 g (4.0 mol) of ortho-nitrotoluene was introduced continuously over 2 hours;

Feed II: 725 g (3.2 mol) of 15% strength $H_2O_2$ were introduced in such a way that no excess bromine was present in the solution. About 2.5 hours were required for this.

After feeding in was complete, stirring was continued at 75° C. for 2 hours, and then the stirrer was switched off and the phases were separated at 75° C. 2146.4 g of organic phase were obtained with the following composition (according to quant. HPLC):
23.6% o-nitrobenzyl bromide
8.4% o-nitrotoluene
7.1% o-nitrobenzal bromide
Yield of o-nitrobenzyl bromide: 58.1% based on o-nitrotoluene b) Preparation of 2-[(N-p-chlorophenyl)-3-pyrazolyloxymethyl]nitrobenzene 101.5 g (0.5 mol) of 95.8% pure 3-hydroxy-N-(p-chlorophenyl)pyrazole, 875 g of 5% strength aqueous KOH and 40.25 g (0.025 mol) of 20% strength aqueous tetrabutylammonium bromide solution were mixed in a 2.5 liter flat flange flask with impeller stirrer (420 rpm) and baffle. This mixture was homogeneous after having been heated to 80° C., and 504 g of the organic phase obtained in stage a) (equivalent to 0.55 mol of o-nitrobenzyl bromide) were metered in over the course of 5 minutes. The mixture was then stirred at 80° C. for one hour and subsequently the contents of the vessel were cooled to below 10° C., reducing the speed of the stirrer to 200 rpm. The residue was filtered, boiled twice in methanol and again filtered, and finally dried under 100 mbar.

Yield 141 g (85.6%) of the required product with a melting point of 147° C.

The following examples show variants of the process of stage a): the solution of o-nitrobenzyl bromide in chlorobenzene obtained in each case can be employed, as indicated in Example 1, directly in the alkylation step b).

Example 2

Use of 2,2'-azobis(2,4-dimethylvaleronitrile) as initiator 13.7 g (0.1 mol) of o-nitrotoluene, 25 g of chlorobenzene, 600 mg (2.7 mmol) of V 65 (supplied by Wako; 2,2'-azobis (2,4-dimethylvaleronitrile)), 300 mg of $H_2SO_4$ and 16.4 g (0.15 mol) of 30% strength hydrogen peroxide were mixed at 45° C. 10 g of 47% strength hydrobromic acid were added dropwise in 75 min, and the mixture was stirred at 45° C. for a further 75 min.

A further 5 g of hydrobromic acid was added, and the mixture was stirred at room temperature for 12 h. Then 3 g of hydrobromic acid and, in two portions, 15.86 g of a solution of chlorobenzene and V 65 (total of 15 g of chlorobenzene+0.86 g (3.9 mmol) of V 65) were added.

Qualitative HPLC of the organic phase after the end of the reaction showed the following composition (data in percentage area):
52.6% o-nitrobenzyl bromide
35.5% o-nitrotoluene
4.3% o-nitrobenzal bromide
6.5% chlorobenzene

Example 3

Bromine as brominating agent

A mixture of 122.7 g of chlorobenzene, 45.5 g of water and 0.6 g (1 mol %) of AIBN was heated to 75° C. After the temperature was reached, a solution of AIBN in 49.8 g (0.36 mol) of o-nitrotoluene was added dropwise over the course of 1 hour and, in parallel, a total of 44.1 g (0.28 mol) of bromine so that the reaction solution remained permanently decolorized (pale yellow/pale orange). Stirring was carried out at 75° C. for 1 hour after the completion of the addition. The organic phase was separated off at 75° C.

174.5 g of organic phase with the following composition:
25.1% o-nitrobenzyl bromide
11.3% o-nitrotoluene
3.1% o-nitrobenzal bromide
Yield of o-nitrobenzyl bromide: 50.7% based on o-nitrotoluene.

Example 4

Bromination of o-nitrotoluene in a continuous process

Feeds per hour:

Feed I:
54.8 g (0.4 mol) of o-nitrotoluene
3.3 g (5 mol %) of AIBN (α,α'-azoisobutyronitrile)
135 g of chlorobenzene Feed II:
81.6 g (0.36 mol) of 15% strength hydrogen peroxide solution Feed III:
62 g (0.36 mol) of 47% strength hydrobromic acid Feeds I to III were fed, by means of weight-controlled metering pumps, in parallel (immersed) into the first reactor, at an internal temperature of 75° C. and at 300 rpm, of a cascade consisting of 3 stirred vessels (capacity about 300 ml) which were connected together by free overflow. The two phases were separated, likewise continuously, in a downstream settler stage at 75° C.

Operation of the system for 18 hours resulted in:

3752.2 g of organic phase with the following composition:

21.5% o-nitrobenzyl bromide
8.9% o-nitrotoluene
4.9% o-nitrobenzal bromide

Yield of o-nitrobenzyl bromide: 51.9% based on o-nitrotoluene

Example 5

More dilute procedure

A mixture of 1500 g of chlorobenzene, 3.3 g (1 mol %) of AIBN and 310.2 g (1.8 mol) of 47% strength hydrobromic acid was heated to 75° C. After the temperature was reached, a solution of 13.1 g (4 mol %) of AIBN in 274 g (2 mol) of o-nitrotoluene was added dropwise over the course of 2 hours, and in parallel a total of 408 g (1.8 mol) of 15% strength hydrogen peroxide so that the reaction solution remained permanently decolorized (pale yellow/pale orange). Stirring was continued at 75° C. for 1 hour after completion of the addition. The organic phase was separated. off at 75° C.

The remaining 1916.2 g of organic phase had the following composition:

14.2% o-nitrobenzyl bromide
4.0% o-nitrotoluene
2.4% o-nitrobenzal bromide

Yield of o-nitrobenzyl bromide: 63% based on o-nitrotoluene

Comparative Examples

1. Reaction of o-nitrobenzal bromide with 3-hydroxy-N-(p-chlorophenyl)pyrazole

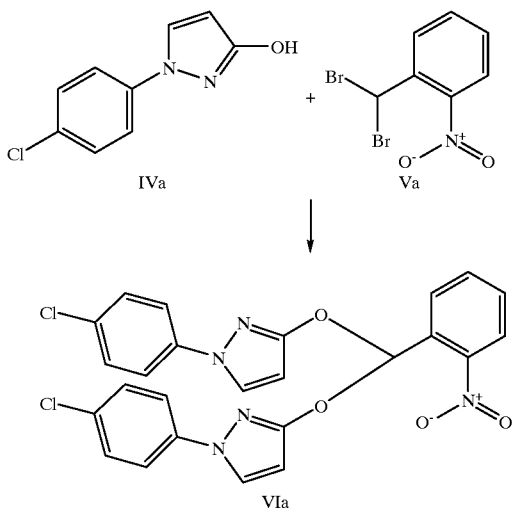

Tetra-n-butylammonium bromide was added to a mixture of 6.8 g of N-(p-chlorophenyl)-3-hydroxypyrazole in 53.7 g of 5% strength potassium hydroxide solution. A solution of 5 g of o-nitrobenzal bromide in 20 g of chlorobenzene was added, and the mixture was heated to 80° C. after stirring for 90 min, the mixture was cooled to 5° C. and the precipitated solid was filtered off with suction. It was washed with cold MeOH and then dried at 50° C. under reduced pressure. This resulted in 6 g of the bispyrazolyl compound VIa as a brownish solid.

A further 2 g of residue were isolated from the mother liquor and, according to GC, comprised 80% VIa.

2. Reaction of a mixture of o-nitrobenzal bromide and o-nitrobenzyl bromide with 3-hydroxy-N-(p-chlorophenyl) pyrazole

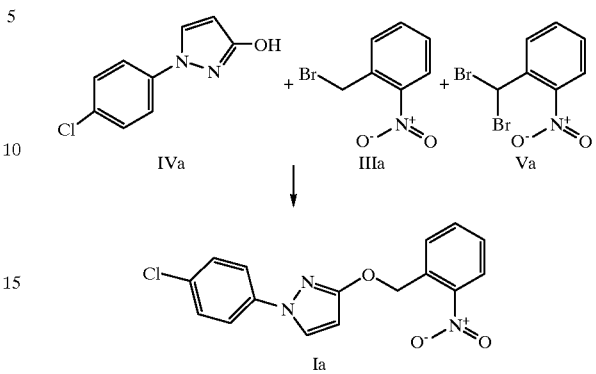

0.8 g of tetra-n-butylammonium bromide was added to a solution of 9.9 g (51 mmol) of 97.2% pure N-(p-chlorophenyl)-3-hydroxypyrazole in 69.6 g of 5% strength KOH and heated to 80° C. At this temperature, a solution of 10.7 g (49.5 mmol) of o-nitrobenzyl bromide and 12.9 g (43.8 mmol) of o-nitrobenzal bromide was added, and the mixture was maintained at this temperature for 90 min. HPLC of the reaction mixture showed that the o-nitrobenzyl bromide and hydroxypyrazole had reacted to give the required benzyl ether Ia, while the o-nitrobenzal bromide was still unchanged even at the end of the reaction.

The yield of Ia isolated after cooling, filtration with suction and washing with methanol in this experiment was 72.3%.

From Comparative Example 1 it would have been expected that the reactivity of o-nitrobenzal bromide is similar to that of o-nitrobenzyl bromide. However, surprisingly, the alkylation takes place with high selectivity, as shown in Comparative Example 2.

We claim:

1. A process for preparing 2-(3-pyrazolyloxymethylene) nitrobenzene derivatives of the formula I

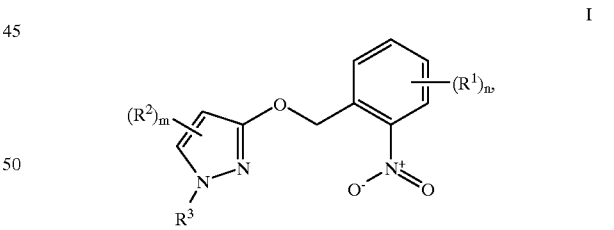

where:

$R^1$ is halogen;
unsubstituted or substituted alkyl or alkoxy;

$R^2$ is cyano, halogen, alkyl, haloalkyl, alkoxy, alkylthio or alkoxycarbonyl;

$R^3$ is unsubstituted or substituted alkyl, alkenyl or alkynyl;
unsubstituted or substituted saturated or mono- or diunsaturated carbocyclyl or heterocyclyl;
unsubstituted or substituted aryl or hetaryl;

m is 0, 1 or 2, it being possible for the substituents $R^2$ to be different when m is greater than 1;

n is 0, 1, 2, 3 or 4, it being possible for the substituents $R^1$ to be different when n is greater than 1;

by bromination of an o-nitrotoluene of the formula II

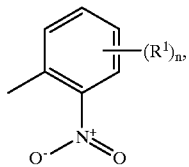

where $R^1$ has the abovementioned meaning, to give the o-nitrobenzyl bromide of the formula III

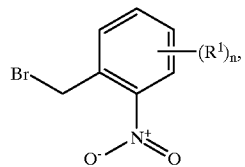

in the presence of a nonpolar, aprotic solvent and subsequent reaction of the resulting solution of III with a 3-hydroxypyrazole of the formula IV

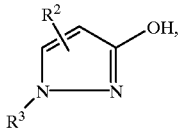

where $R^2$ and $R^3$ have the abovementioned meanings, in the presence of a base, wherein the solution of the o-nitrobenzyl bromide III resulting from the bromination is reacted further with IV, in the solvent used, directly without intermediate isolation of the o-nitrobenzyl bromide III.

2. A process as claimed in claim 1, wherein the molar ratio of o-nitrobenzyl bromide III to 3-hydroxypyrazole IV employed is 1–1.2.

3. A process as claimed in claim 1, wherein the bromination to give the o-nitrobenzyl bromide III is carried out continuously.

4. A process as claimed in claim 1, wherein both the bromination to give o-nitrobenzyl bromide III and the subsequent alkylation to give the 2-(3-pyrazolyloxymethylene) nitrobenzene I are carried out continuously.

5. A process as claimed in claim 1, wherein the bromination to give the o-nitrobenzyl bromide III is carried out in the presence of an azo carbonitrile or azo carboxylic ester as initiator.

6. A process as claimed in claim 5, wherein the bromination to give the o-nitrobenzyl bromide III is carried out with hydrobromic acid, with inorganic bromides dissolved in water, or with elemental bromine in the presence of an oxidizing agent.

7. A process as claimed in claim 6, wherein hydrogen peroxide is employed as oxidizing agent.

8. A process as claimed in claim 1, wherein the bromination and the alkylation are carried out in a two-phase system consisting of aqueous and organic phase.

* * * * *